US011084039B2

(12) United States Patent
Davies et al.

(10) Patent No.: US 11,084,039 B2
(45) Date of Patent: Aug. 10, 2021

(54) MICROFLUIDIC ANALYSIS SYSTEM (71) Applicant: STOKES BIO LIMITED, Limerick (IE)

(72) Inventors: Mark Davies, Limerick (IE); Tara Dalton, Limerick (IE)

(73) Assignee: STOKES BIO LTD., Limerick (IE)

( * ) Notice: Subject to any disclaimer, the term of this patent is extended or adjusted under 35 U.S.C. 154(b) by 0 days.

(21) Appl. No.: 15/429,765

(22) Filed: Feb. 10, 2017

(65) Prior Publication Data

US 2017/0216846 A1 Aug. 3, 2017

Related U.S. Application Data (60) Division of application No. 14/486,987, filed on Sep. 15, 2014, now abandoned, which is a continuation of application No. 12/093,132, filed as application No. PCT/IE2007/000015 on Feb. 7, 2007, now abandoned.

(60) Provisional application No. 60/765,670, filed on Feb. 7, 2006.

(51) Int. Cl.
*B01L 7/00* (2006.01)
*B01L 3/00* (2006.01)
*G01N 21/64* (2006.01)
*C12Q 1/686* (2018.01)

(52) U.S. Cl.
CPC ......... *B01L 7/525* (2013.01); *B01L 3/502715* (2013.01); *B01L 3/502784* (2013.01); *C12Q 1/686* (2013.01); *G01N 21/6428* (2013.01); *B01L 3/5027* (2013.01); *B01L 2200/0673* (2013.01); *B01L 2300/0627* (2013.01); *B01L 2300/0654* (2013.01); *B01L 2300/0838* (2013.01); *B01L 2300/0867* (2013.01); *B01L 2300/18* (2013.01); *B01L 2300/185* (2013.01); *B01L 2300/1822* (2013.01); *B01L 2400/0487* (2013.01); *G01N 2201/0826* (2013.01); *G01N 2201/0833* (2013.01)

(58) Field of Classification Search
CPC ............... B01L 7/525; B01L 3/502715; B01L 3/502784; B01L 2300/185; B01L 3/5027; B01L 2300/0627; B01L 2200/0673; B01L 2300/18; C12Q 1/686
See application file for complete search history.

(56) References Cited

U.S. PATENT DOCUMENTS

| 5,270,183 | A | 12/1993 | Corbett et al. |
| 5,675,155 | A * | 10/1997 | Pentoney, Jr. ... G01N 27/44721 204/452 |
| 5,736,314 | A | 4/1998 | Hayes et al. |
| 5,779,977 | A | 7/1998 | Haff et al. |
| 5,720,923 | A | 10/1998 | Haff et al. |
| 5,827,480 | A | 10/1998 | Haff et al. |
| 5,952,202 | A | 9/1999 | Aoyagi et al. |
| 6,033,880 | A | 3/2000 | Haff et al. |
| 7,622,076 | B2 | 11/2009 | Davies et al. |
| 2001/0042712 | A1 | 11/2001 | Battrell et al. |
| 2001/0046701 | A1 | 11/2001 | Schulte et al. |
| 2002/0185183 | A1 | 12/2002 | O'Connor et al. |
| 2003/0128910 | A1 | 7/2003 | Naghieh et al. |
| 2004/0180346 | A1 | 9/2004 | Anderson et al. |
| 2005/0186585 | A1 | 8/2005 | Juncosa et al. |
| 2005/0202489 | A1 | 9/2005 | Cho et al. |
| 2005/0221373 | A1 | 10/2005 | Enzelberger et al. |
| 2005/0266448 | A1 | 12/2005 | Hagiwara et al. |
| 2006/0127889 | A1 | 6/2006 | Stanton et al. |
| 2006/0257853 | A1 | 11/2006 | Herman |
| 2007/0039866 | A1 | 2/2007 | Schroeder |
| 2007/0062583 | A1 | 3/2007 | Cox et al. |
| 2007/0068573 | A1 | 3/2007 | Cox et al. |
| 2007/0141593 | A1 | 6/2007 | Lee |
| 2008/0280331 | A1 | 11/2008 | Davies |

(Continued)

FOREIGN PATENT DOCUMENTS

| EP | 1544586 | 6/2005 |
| EP | 1574586 | 9/2005 |

(Continued)

OTHER PUBLICATIONS

Zhang et al. Biotechnology Advances 2006; 24: 243-284. (Year: 2006).*
Sun et al. Sensors and Actuators B 2002; 84: 283-289. (Year: 2002).*
Vogelstein et al. Proceedings of the National Academy of Sciences, USA 1999; 96: 9236-9241.*
Chabert et al. Analytical Chemistry 2006; 78: 7722-7728. (Year: 2006).*
Schneegass, I. and Kohler, J.M. Reviews in Molecular Biotechnology 2001; 82: 101-121. (Year: 2001).*
Dorfman et al. Analytical Chemistry 2005; 77: 3700-3704. (Year: 2005).*

(Continued)

*Primary Examiner* — Angela M. Bertagna
(74) *Attorney, Agent, or Firm* — Jones Robb, PLLC (57) ABSTRACT A biological sample analysis system including a sample preparation system forming droplets of segmented sample separated by a carrier fluid immiscible with the sample. The droplets include reaction mixtures for amplification of at least one target nucleic acid. A thermal cycling device having a sample block having a plurality of controlled thermal zones, and a containment structure in thermal communication with the plurality of controlled thermal zones. The containment structure receives and contains the droplets of segmented sample separated by the immiscible carrier fluid from the sample preparation system. A controller for controlling a temperature in each thermal zone of the sample block. A detection system detects electromagnetic radiation emitted from each of the droplets individually from the queue of droplets as they flow past the detection system. A positioning system to facilitate moving a queue of the droplets in the thermal cycling device relative to the detection system.

27 Claims, 9 Drawing Sheets

(56) References Cited

U.S. PATENT DOCUMENTS

| | | | |
|---|---|---|---|
| 2009/0226972 A1* | 9/2009 | Beer | F28F 3/12 435/91.2 |
| 2009/0317874 A1 | 12/2009 | Dale et al. | |
| 2010/0294048 A1 | 11/2010 | McGuire et al. | |
| 2010/0304446 A1 | 12/2010 | Mark et al. | |

FOREIGN PATENT DOCUMENTS

| | | | |
|---|---|---|---|
| EP | 1584692 | 10/2007 | |
| WO | 2001/007159 | 1/2001 | |
| WO | 2003/016558 | 2/2003 | |
| WO | 2004/024330 | 3/2004 | |
| WO | 2004/079002 | 9/2004 | |
| WO | 2005/002730 | 1/2005 | |
| WO | WO-2005075683 A1 * | 8/2005 | B01L 7/525 |
| WO | 2005/103106 | 11/2005 | |
| WO | 2006/089192 | 8/2006 | |
| WO | 2007/091228 | 8/2007 | |
| WO | 2007/091230 | 8/2007 | |

OTHER PUBLICATIONS

Baechi et al. Biomedical Microdevices 2001; 3: 183-190 (Year: 2001).*

Cui, et al., "Optical Particle Detection Integrated in a Dielectrophoretic Lab-on-a-Chip", *Journal of Micromechanics and Microengineering*, 12(1), 2002, 7-12.

Hashimoto, Masahiko et al., "Rapid PCR in a continuous flow device. Lab on a Chip (2004)", Aug. 13, 2004, 634-345.

Kopp, M.U. et al., "Chemical Amplification: Continuous-Flow PCR on a Chip", *Science*, vol. 280, May 18, 1998, 1046-1048.

Kricka, L J. et al., "Microchip PCR", 377 *Analytical and Bioanalytical Chemistry*, 377, pp. 820-825, 2003.

Liu, et al., "DNA Amplification and Hybridization Assays in Integrated Plastic Monolithic Devices", *Analytical Chemistry*, 74, 2002, 3063-3070.

Panaro, et al., "Surface effects on PCR reactions in multichip microfluidic platforms", *Biomedical Devices*, 6(1), 2004, 75-80.

PCT/IE2007/000015, International Search Report, dated May 7, 2007, 3 pgs.

PCT/US2011/030047, International Search Report, 3 pgs, dated Dec. 22, 2011.

PCT/US2011/030047, Written Opinion dated Dec. 22, 2011, 6 pgs.

Song, Helen et al., "A microfluidic system for controlling reaction networks in time", *Angewandte Chemie International Edition*, vol. 42, No. 7, 2003, 768-772.

Taylor, Theresa B. et al., "Optimization of the Performance of the Polyermase Chain Reaction in Silicon-Based Microstructures", vol. 25, No. 15, *Nucleic Acids Research*, pp. 3164-3168, 1997.

Woolley, et al., "Functional Integration of PCR Amplification and Capillary Electrophoresis in a Microfabricated DNA Analysis Device", *Analytical Chemistry*, 68, 1996, 4081-4086.

Obeid et al. Anal. Chem. 2003; 75: 288-295.

PCT/IE2007/000015, International Preliminary Report on Patentability, dated Aug. 12, 2008.

PCT/IE2007/000015, Written Opinion of the International Searching Authority, dated Aug. 12, 2008, 6 pgs.

PCT/IE2007/000015, International Preliminary Report on Patentability, dated Aug. 12, 2008, first page only.

EP Communication issued in Application No. 11 760 338.1, dated Mar. 7, 2018.

* cited by examiner

Three fiber illumination (left) and detection (right) in the thermal cycler.

MICROFLUIDIC ANALYSIS SYSTEM

CROSS-REFERENCE TO RELATED APPLICATIONS

This application is a divisional of U.S. application Ser. No. 14/486,987 filed Sep. 15, 2014 (now abandoned), which is a continuation of U.S. application Ser. No. 12/093,132 filed May 20, 2008 (now abandoned), which is a 371 of International Application No. PCT/IE2007/000015 filed Feb. 7, 2007 (now expired), and claims the benefit of U.S. Provisional Application No. 60/765,670 filed Feb. 7, 2006, all of which are herein incorporated by reference in their entirety.

FIELD OF THE INVENTION

The invention relates to analysis of samples to which thermal cycling is applied for nucleic acid amplification, such as in the quantitative polymerase chain reaction (qPCR).

PRIOR ART DISCUSSION

Conventionally, nucleic acid amplification has involved providing an array of samples in an assay plate and thermally cycling the plate reaction vessel. This, however, involves the laborious task of loading the samples and preparing a fresh assay well plate.

It is known to provide a thermal cycler for nucleic acid amplification, and U.S. Pat. Nos. 5,270,183, 2005/075683, 6,033,880, and 6,814,934 describe thermal cycler analysis systems.

The prior systems suffer from being complex, both in physical and control terms. For example, in the system of U.S. Pat. No. 6,033,880 it is necessary to rotate heat exchangers into desired positions, and in the system of U.S. Pat. No. 6,814,934 it is necessary to heat and cool a reaction vessel.

The invention is directed towards providing an improved thermal cycler system in which a requirement to heat and cool a reaction vessel is avoided. Another object is to achieve improved detection efficiency.

SUMMARY OF THE INVENTION

According to the invention, there is provided a microfluidic analysis system comprising a thermal cycling device, the device having a plurality of fixed thermal zones and a fixed conduit passing through the thermal zones, a controller for maintaining each thermal zone including its section of conduit at a constant temperature, means for flowing a series of droplets through the conduit so that each droplet is thermally cycled, and a detection system for detecting electromagnetic radiation from droplets at a plurality of said thermal cycles.

In one embodiment, the conduit is in a single plane.
In one embodiment, the conduit comprises a channel.
In one embodiment, the thermal zones are mutually thermally insulated.
In one embodiment, the flow conduit comprises a channel and a capillary tube inserted into the channel.
In one embodiment, the capillary has a circular cross-section.
In one embodiment, the channel and capillary are configured to receive a refractive index-matching liquid in the channel and at least partly surrounding the capillary.

In another embodiment, the channel has a depth greater than that of the capillary.
In one embodiment, the detection system comprises optics for focusing incident light radiation.
In one embodiment, the detection system comprises optics for filtering incident radiation.
In one embodiment, the detection system comprises optics for filtering emitted radiation.
In another embodiment, the detection system performs scans along a direction to detect radiation from a plurality of cycles in a pass.
In one embodiment, the detection system performs simultaneous detection of emitted light from a plurality of cycles.
In one embodiment, there is an air gap between adjacent thermal zones.
In one embodiment, said air gap is adjustable.
In one embodiment, the flow conduit passes through a hot thermal zone for a length before a first cycle, providing a denaturation zone.
In another embodiment, the detection system comprises a plurality of optic fibres for point illumination of each of a plurality of cycles.
In one embodiment, the detection system comprises a plurality of optic fibres for point detection of each of a plurality of cycles.
In one embodiment, the detection system comprises a rotating filter for cyclic filtering of incident or emitted light.
In one embodiment, the conduit is in a serpentine pattern of multiple folds, each fold extending through a plurality of thermal zones.
In a further embodiment, the system comprises a plurality of thermal cycling devices arranged in parallel.
In one embodiment, the thermal cycling devices are interconnected to form a physical unit.
In one embodiment, the detection system performs simultaneous detection of emitted light from a plurality of cycles from a plurality of thermal cycling devices.

DETAILED DESCRIPTION OF THE INVENTION

BRIEF DESCRIPTION OF THE DRAWINGS

The invention will be more clearly understood from the following description of some embodiments thereof, given by way of example only with reference to the accompanying drawings in which.

DESCRIPTION OF THE EMBODIMENTS

An analysis system of the invention is based on microfluidics technology. Microfluidic devices themselves have dimensions ranging from several millimetres to micrometers. Typically one of the components or dimensions of the device, such as a channel in the device, is of the order of micrometers.

The polymerase chain reaction, or PCR, is a powerful technique used to amplify low concentrations of specific DNA sequences to levels which may be detected. PCR can be used to achieve a billionfold increase in target sequence copy number by thermally cycling a specific chemical mix. This makes the PCR method extremely sensitive as it can detect a single DNA molecule in a sample.

Figure 1:
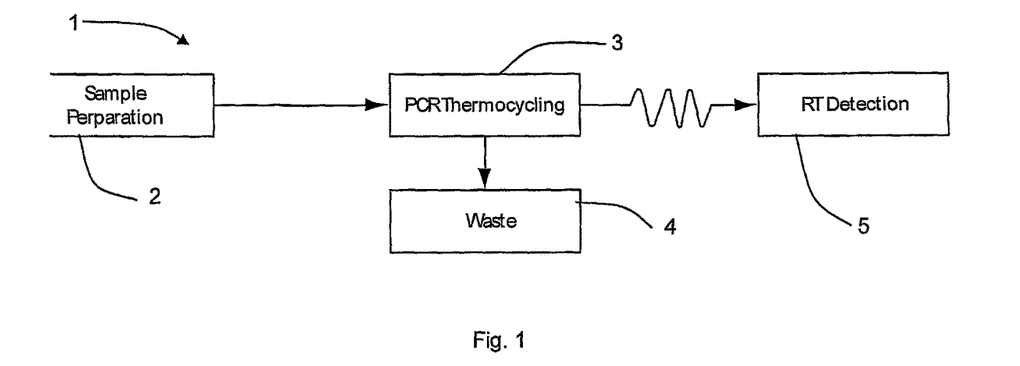
FIG. 1 is a block diagram of an analysis system of the invention.

FIG. 1 shows an analysis system 1 for PCR. It has a sample preparation stage 2, a thermal cycling stage 3 for PCR, a waste outlet 4, and a real time detection stage 5 to achieve qPCR.

Figure 2:
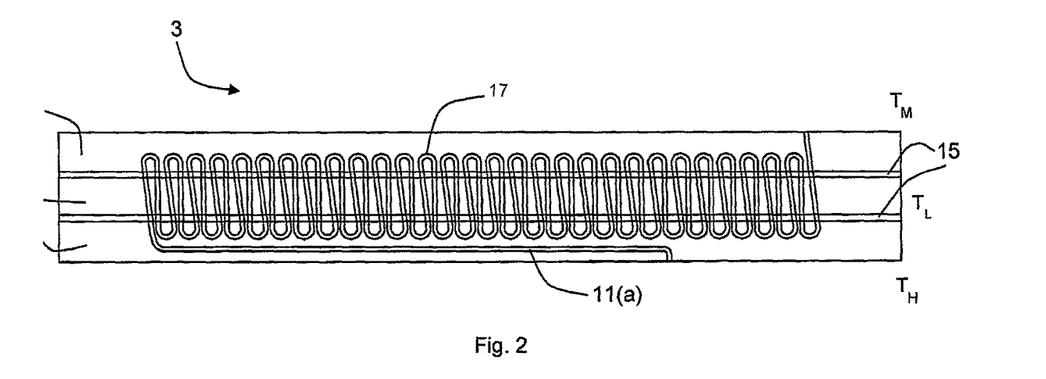
FIG. 2 is a plan view of a thermal cycler of the system having three thermal zones.

FIG. 2 shows the thermal cycler 3. It has a planar two dimensional serpentine channel 17 which is machined into a block which is segmented into three thermal zones 11, 12, and 13 separated by 1 mm air gaps 15. The three thermal zones are controlled to achieve the three individual temperature zones required for the PCR reaction. Each thermal section is controlled by continuous temperature sensing and a PID feedback control system. Circular tubing is laid into a channel in a block of Al material to ensure biocompatibility for the reaction. The circular tubing gives a smooth internal surface and has no sharp edges to restrict the reaction. This results in stable, spherical sample droplets. The tubing is embedded in the machined channel which results in high heat transfer from the block to the sample.

Figure 3:
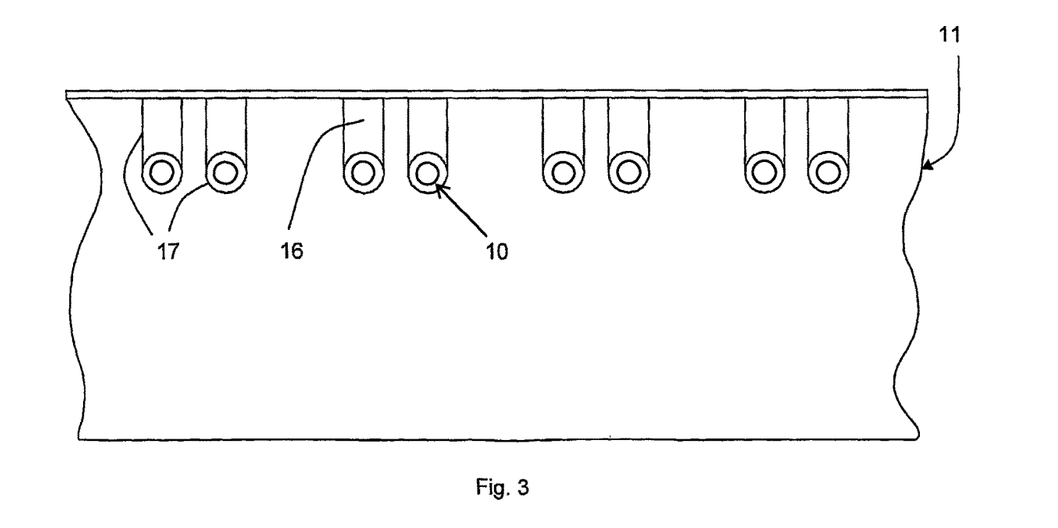
FIG. 3 is a vertical cross section.

FIG. 3 shows the machined channel 17 which contains the tubing 10 and a refractive index matching solution. The machined channel 17 enables the introduction of the refractive index matching solution 16 as it is considerably deeper than the diameter of the tubing 10. The solution 16 covers the remainder of the channel above the tubing 10 and results in high accuracy detection through the tubing. An example of the refractive index matching with the tubing is the use of a glycerine dilution solution. The device is planar in design, which provides the ability for continuous detection throughout the thermal cycling process. This enables real time quantitative detection (termed "qPCR"). The assembly may be sealed using optical quality glass or thin film adhesive.

Figure 4:
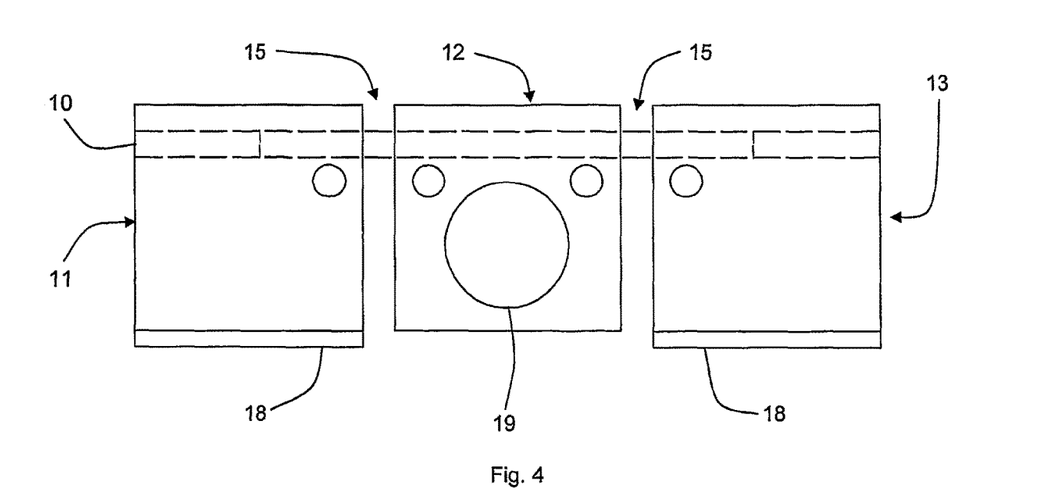
FIG. 4 is an end view of the thermal cycler.

FIG. 4 shows thermal foil heaters 18 for heating the blocks of the thermal zones 11 and 13. The low temperature thermal zone 12 has a water channel 19 for maintaining a uniform low temperature. The thermal sections are controlled by temperature sensor monitoring and a PID feedback control system.

The inlet to the analysis system 1 is connected to the PCR preparation system 2. During sample preparation the double-stranded DNA sample is combined with two oligonucleotide primers. The sample is segmented into droplets which are wrapped in immiscible oil. The oil avoids cross contamination between the sequential droplets and carry-over contamination within the device. This configuration avoids the need to purge the system between different samples. A queue of different droplets from the preparation system may be passed through the thermal cycler 3 directly. The block and tubing are stationary so only the wrapped samples and oil solution move in the thermal cycle system. Each thermal zone 11, 12, and 13, including the Al block and the embedded tubing 10, is an isothermal zone. Each zone is controlled to be isothermal with respect to time. The velocity of the sample through the device is defined by the control of the velocity of the carrier fluid. This is controlled by an external pumping system. The velocity may then be varied to control the residency time of the sample in each temperature zone 11-13.

The sample passes to the PCR thermal cycler 3 within the carrier fluid and through an initial denaturation zone 11(*a*) before commencement of thermal cycling. The sample passes into the high thermal section 11(*a*) where it is first separated into single stranded DNA in a process called denaturation at a temperature $T_H$.

The sample flows through the device at a steady controlled velocity to the second temperature $T_L$, where the hybridisation process takes place, during which the primers anneal to the complementary sequences of the sample. Finally, as the sample flows through the third and medium temperature zone, $T_M$, the polymerase process occurs when the primers are extended along the single strand of DNA with a thermostable enzyme. The sample undergoes the same thermal cycling and chemical reaction as it passes through N amplification cycles of the complete thermal device. This results in a maximum two-fold amplification after each cycle and a total amplification of $$I(1+E)^N$$

where I is the initial product, E is the efficiency of the reaction and N is the number of cycles.

EXAMPLE

Fluorescent probes are contained in each sample droplet. The fluorescence level is detected in each droplet at each cycle. This quantitative analysis provides information on the specific concentration in the sample.

The three thermal zones are controlled to have temperatures as follows:

Zone 11 95° C. ($T_H$),
Zone 12 55° C. ($T_L$),
Zone 13 72° C. ($T_M$).

The prepared sample droplets, wrapped in the carrier fluid, enter the inlet to the thermal cycler at the controlled velocity. The sample then passes to the PCR thermal cycler 3 within the carrier fluid and through the initial denaturation zone 11(*a*) before thermal cycling. The initial preheat is an extended zone to ensure the sample has denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature zone 12, of approximately 55° C., where the hybridisation process takes place, during which the primers anneal to the complementary sequences of the sample. Finally, as the sample flows through the third medium temperature zone 13, of approximately 72° C., the polymerase process occurs when the primers are extended along the single strand of DNA with a thermostable enzyme. The sample undergoes the same thermal cycling and chemical reaction as it passes through each thermal cycle of the serpentine pattern. The total number of cycles in the device is easily altered by an extension of block length and tubing. The system 1 has a total cycle number of 30 in this embodiment. The device may be extended to a longer thermal cycler or a combination of two thermal cyclers to achieve a greater cycle number.

Figure 5:
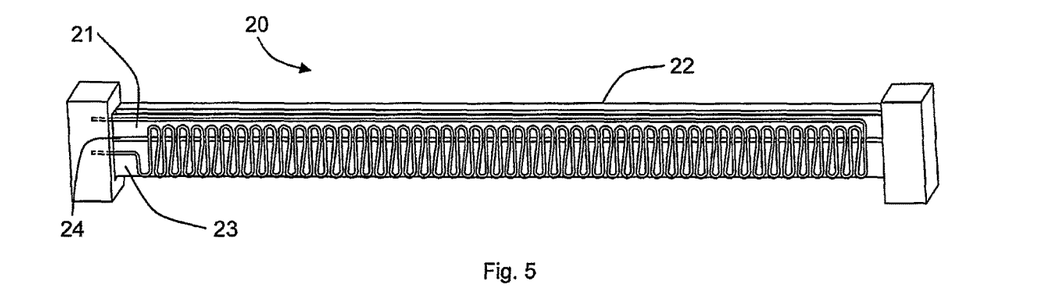
FIG. 5 is a perspective view of an alternative thermal cycler, having only two thermal zones.

Referring to FIG. 5, in a cycler 20 there are two temperature zones 21 and 23, separated by an insulated air gap 24 to provide the correct temperatures zones necessary for the PCR reaction. The zone 21 is heated by a thermal foil heater 22, and the zone 23 is heated by natural convection from the top block defining temperature zone 21. Again, the two zones including the embedded tubing are stationary throughout the reaction and hence isothermal with respect to time.

The section temperatures are:
Zone 21, 95° C. ($T_H$),
Zone 23, 60° C. ($T_L$),

The position of the lower block may be adjusted by increasing the insulation gap 24. This adjusts the temperature of the zone 23. The tubing protrudes below the edge of the bottom aluminium block when it is laid in the channel, providing an inspection window. This is advantageous for the quantitative detection as it provides optical access to the tubing in two planes.

The prepared sample droplets, wrapped in the carrier fluid, enter the inlet to the thermal cycler at the controlled velocity. Different droplets are queued in the sample preparation device and flow into the thermal cycler in a queue of droplets. A suggested optimum configuration for droplet stability, and to avoid contamination, is a droplet diameter of approximately 400 μm, and a spacing of the same distance. The wrapped nature of the droplets enables continuous flow of alternative droplets without any contamination. This also removes the requirement to purge the system after each reaction. The sample then passes to the PCR thermal cycler within the carrier fluid and through an initial preheat zone before entering the thermal cycling. The preheat zone is necessary for some chemistry for activation and also to ensure the sample is fully denatured before the thermal cycling reaction begins. The preheat dwell length results in approximately 10 minutes preheat of the droplets at the higher temperature. The sample continues into the high temperature zone, of approximately 95° C., where the sample is first separated into single, stranded DNA in a process called denaturation. The sample then flows through the device to the low temperature zone, of approximately 60° C., where the hybridisation process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing. The system has a total cycle number of 50 in this embodiment. The device may be extended to a longer thermal cycler or a combination of two thermal cyclers to achieve a greater cycle number. Real time detection is applied to the device to provide quantitative polymerase chain reaction (qPCR). This involves the use of fluorescent probes such as SYBR Green or Taqman probes.

Figure 6:
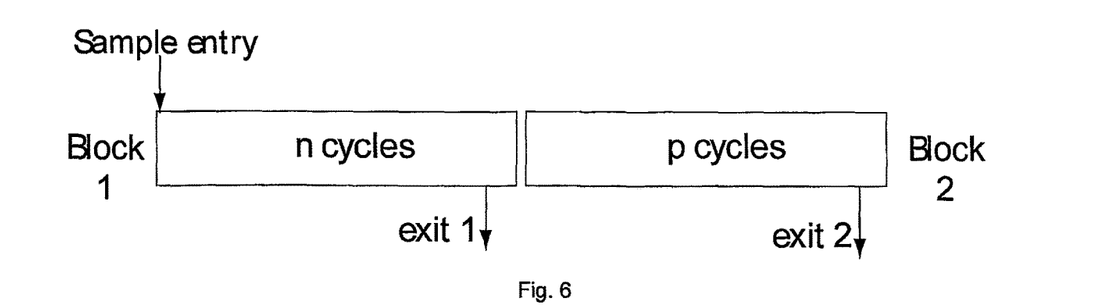
FIG. 6 is a diagram showing an arrangement with two exits, providing a choice of n cycles or n+p cycles.

For a larger cycle number, or an optional extension to the cycle number, the device may be divided into two sections; one with n cycles and one with p cycles as shown in FIG. 6. The combination of the two devices enables a PCR total cycle number of n, p or (n+p) depending on the tubing configuration and the heater control. Each block may be separately controlled to allow for individual use or combined use. Therefore, the cycle number of the device may be varied for greater versatility.

Case 1: Block 2 is thermally controlled and block 1 is uncontrolled (no temperature input). The sample may then enter block 1, flow through the device and exit the thermal cycler at exit 2 following p cycles.

Case 2: The two blocks are thermally controlled. Then the sample enters block 1, flows through the device and exits at exit 2 after (n+p) cycles.

Case 3: The tubing is changed to use exit 1. The sample enters block 1, flows through block 1 and then exits at exit 1 following n cycles.

Figure 7:
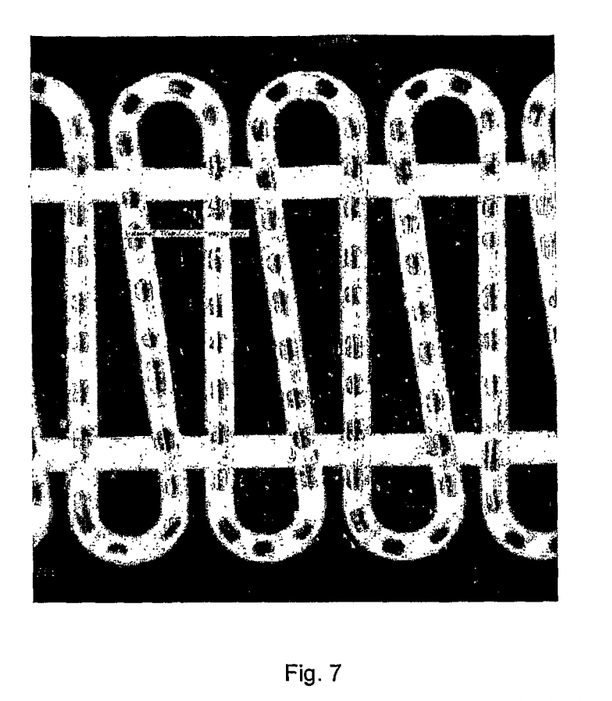
FIG. 7 is a photograph showing droplets flowing in a number of cycles of the thermal cycler having three thermal zones.

FIG. 7 shows a photograph of segmented droplets flowing though the thermal cycler shown in FIG. 2. The system allows for the quadruplicate amplification of a sample. The design avoids cross contamination between successive samples and the planar device allows full field detection during the thermal cycling.

A suggested optimum configuration for droplet stability, and to avoid contamination, is a droplet diameter of approximately 400 μm and a spacing of the same distance. This configuration is suggested for the tubing used in this embodiment which has an internal diameter of 400 μm. The wrapped nature of the droplets enables continuous flow of alternative droplets without any contamination. This also removes the requirement to purge the system.

Detection System

Quantitative PCR, or Q-PCR, is a variant of the basic PCR technique. The present Q-PCR methods use fluorescent probes to monitor the amplification process as it progresses. The SYBR Green 1 dye is commonly used for the fluorescent detection of double-stranded DNA generated during PCR. The dye exhibits a peak excitation maximum at 497 nm and a peak emission maximum at 520 nm. Taqman probes may also be used which are a more target specific probe. The Taqman probes have different excitation and emission wavelengths but one example is the FAM labelled probe which has a peak excitation of 488 nm and an emission of 520 nm.

Through the analysis of the cycle-to-cycle change in fluorescence signal important information regarding the DNA sample may be obtained. This is done by illuminating the sample and detecting the resulting fluorescence. Different product concentration will demonstrate fluorescence amplification at difference cycle numbers. Through the analysis of the behaviour of the sample the characterisation is possible.

Figure 8:
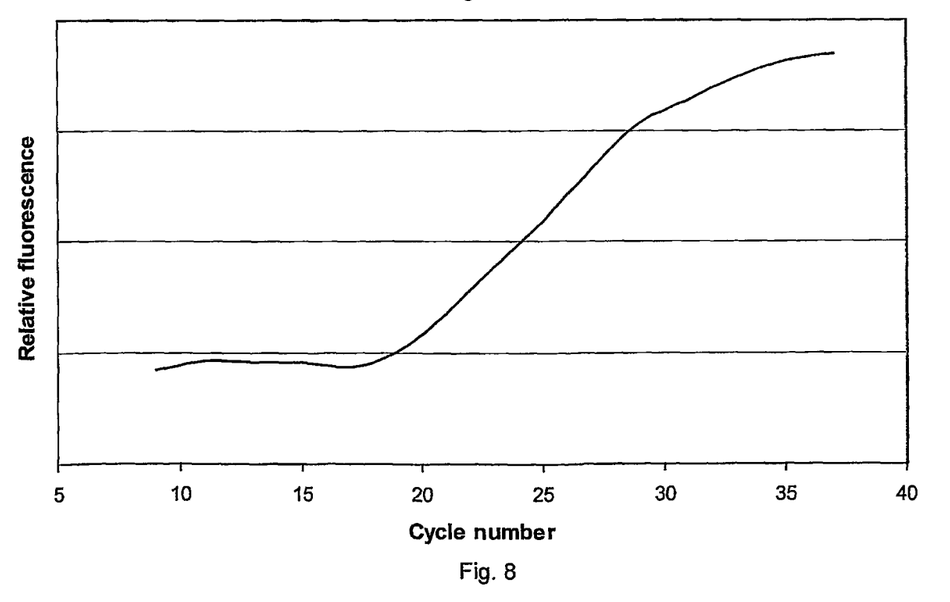
FIG. 8 is a plot illustrating fluorescence characteristics for detection.

FIG. 8 demonstrates an example of a fluorescence amplification curve. This was demonstrated using a Taqman probe. There is little change in the fluorescent signal after the first number of thermal cycles. This defines the baseline for the amplification plot. Fluorescence intensity levels above this baseline represent amplification of PCR product. A fluorescent threshold can be fixed above this baseline that defines the threshold cycle, or Ct, for each reaction. The threshold cycle is defined as the fractional cycle number at which the fluorescence passes above a fixed threshold. Ct is observed in the early exponential stages of amplification. The higher the starting DNA template concentration, the sooner a significant increase in fluorescence is observed. Therefore the starting DNA concentration may be determined by the real time fluorescent detection of the amplifying sample.

Figure 9:
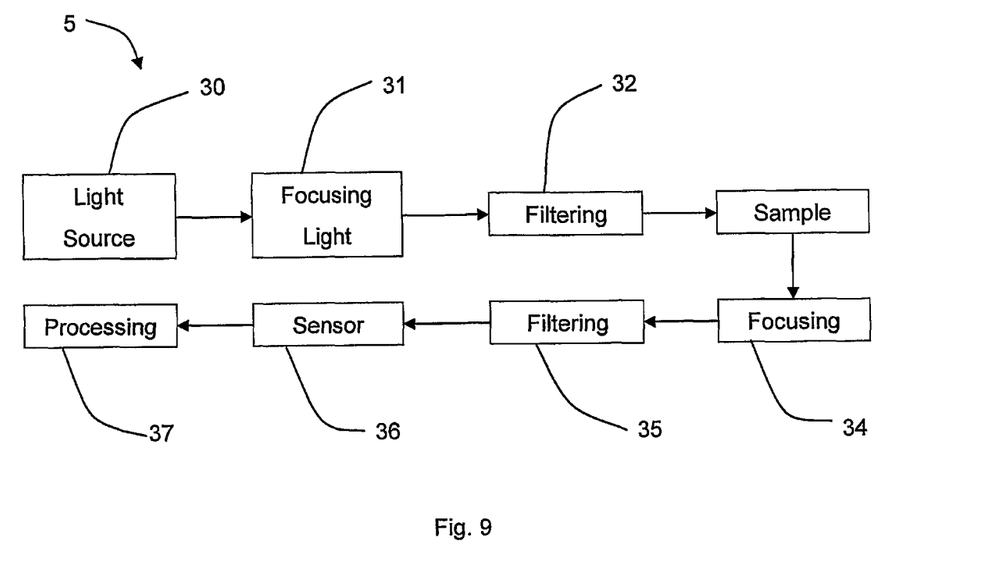
FIG. 9 is a block diagram of a detection system of the analysis system.

Referring to FIG. 9 the detection system 5 comprises:
30, light source;
31, optics for focusing the incident light;
32, filters for filtering the incident light;
34, focusing optics for focusing fluorescence emitted by the sample;
35, filter optics for filtering the emitted fluorescence;
36, sensor electronics; and
37, processing electronics.

The choice of light source is dependent on the remainder of the detection system but there are many options including filtered white light, specific wavelength laser or laser diode. Fibre optics may also be incorporated for light transport. The filtering is dependent on the light source and detection system but commercially available filter components may be used.

Figure 10:
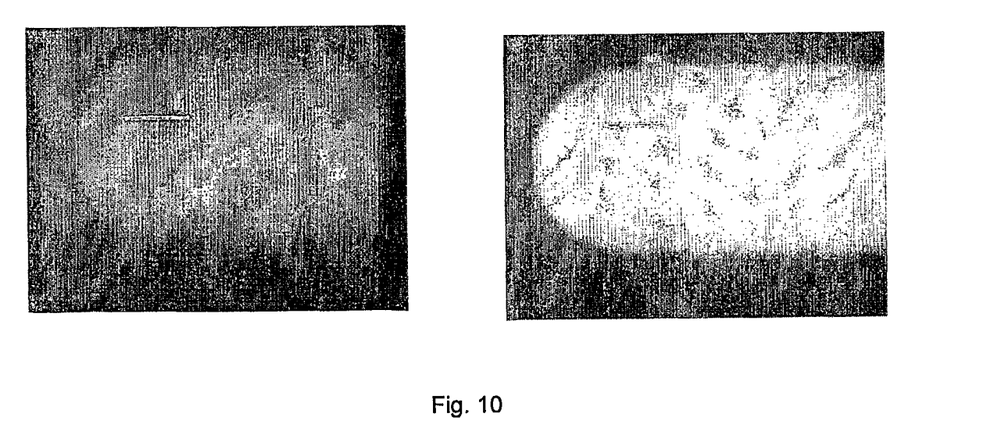
FIG. 10 is a pair of photographs, showing negative and positive fluorescence detection, from left to right.

If a detection indicator is used this will be provided in the sample preparation system. The use of SYBR green fluorescence is demonstrated in FIG. 10. This demonstrates the use of the fluorescence for the amplification detection in the tubing used in the thermal cycler. The increase of fluorescence with increased sample amplification may be seen from the images.

The detection sensor used is dependent on the field of view required and the illumination wavelength chosen. Detector options include CCD, CMOS, photodiode and photomultipliers As the choice and combination of elements chosen are dependent on the overall detection system design and implementation a number of systems are outlined below.

In summary, the system amplifies a DNA sample in a polymerase chain reaction comprising the following steps:
a. Introducing spherical droplets of sample contained in an immiscible carrier fluid to the thermal cycler
b. Passing the sample through circular tubing to provide a smooth internal surface and no sharp edges allowing for most stable, spherical droplets.
c. Controlling the three thermal zones for successful reaction
d. Controlling the carrier fluid velocity by an external pumping system to achieve the target residency times in the thermal zones
e. Passing the sample through the (three) thermally controlled zones to successfully achieve DNA sample amplification.
f. Repeating step e the necessary number of times to achieve the desired sample amplification
g. The quantitative detection of the amplification process.

The device is planar in design, enabling continuous quantitative PCR and multiple levels for any desired level of parallelism.

The channel design enables manipulation for refractive index matching within the device for high quality detection. Also, the channel design results in high heat transfer efficiency by embedding the tubing within the channel. As the droplets are wrapped in an immiscible oil, sequential sample contamination or cross-over contamination within the device is avoided.

Each thermal zone is controlled by continuous temperature sensing and a PID feedback control system. In the embodiments there are 30 cycles and the particular temperatures defined achieved successful denaturation, annealing and hybridisation reactions.

Figure 11:
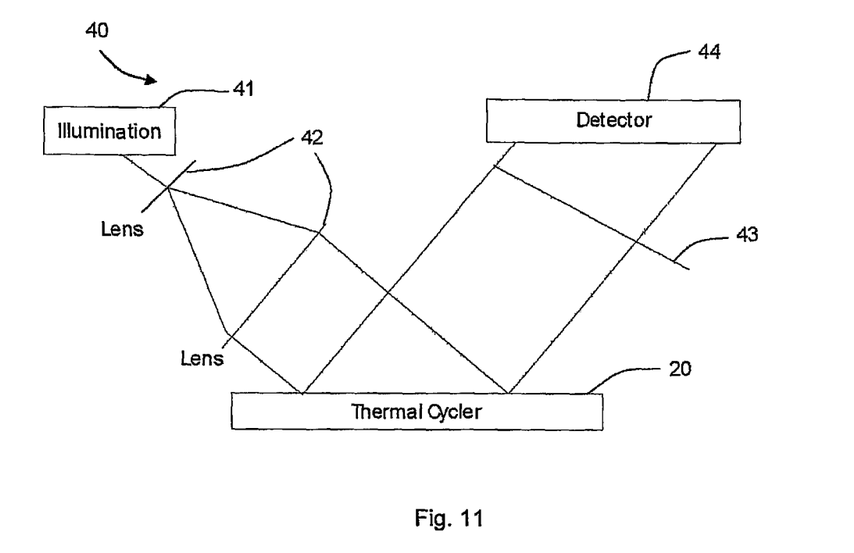
FIGS. 11 to 14 are diagrams showing alternative detection arrangements.
Figure 12:
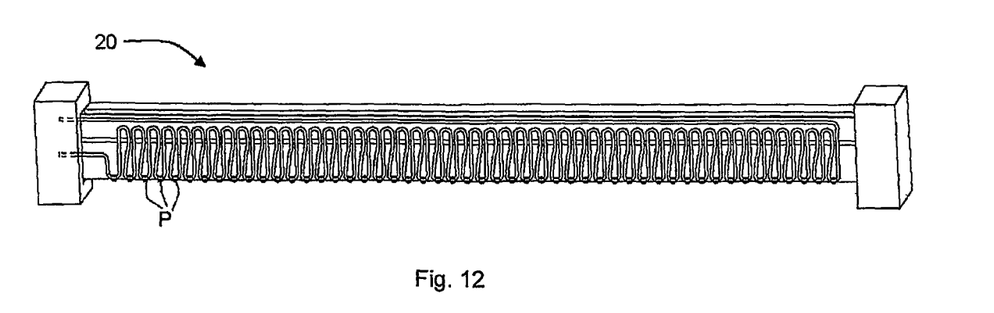

FIG. 11 shows a full field detection system 40 which allows real time detection without any moving parts. The system 40 comprises an illuminator 41 and lenses 42 illuminating the cycler 20, and a filter 43 for impingement of emission onto a detector 44. This enables global measurement of the full thermal cycler 20 or the specific measurement at localised points along the thermal cycler. This is demonstrated in a view of the detection system in FIG. 12, in which individual measurements are taken for a linear series of points P. The detection measurement point in each cycle is dependent on the fluorescent probes used for qPCR. Some probes fluoresce at any point in the reaction whilst others only fluoresce at the annealing/extension stage.

Figure 13:
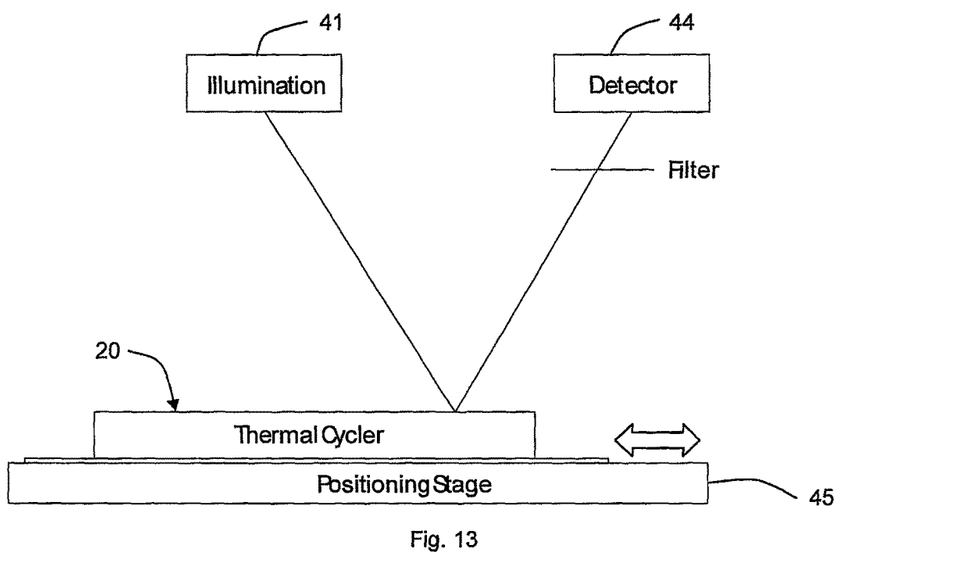
Figure 14:
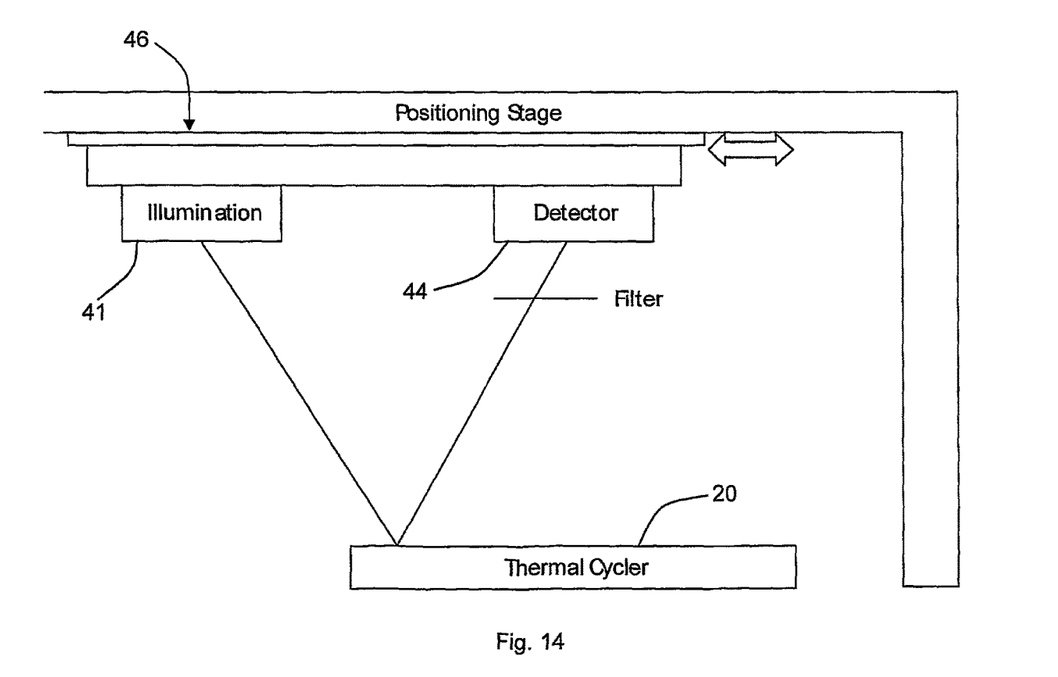

FIGS. 13 and 14 are scanning detection systems for two alternative configurations. These systems also allow real time detection by moving the relative positions of the detection system and the thermal cycler. In the system of FIG. 13 a positioning stage 45 moves the cycler 20, whereas in the system of FIG. 14 a positioning system 46 moves the illuminator 41 and the detector 44.

Whilst the above describes a single thermal cycler, the same movement may be applied to multiple thermal cyclers by simple adding detection and illumination points. The angle of illumination and detection, or orientation of the optical fibers, may also be altered to facilitate multiple thermal cycler real time detection.

Figure 15:
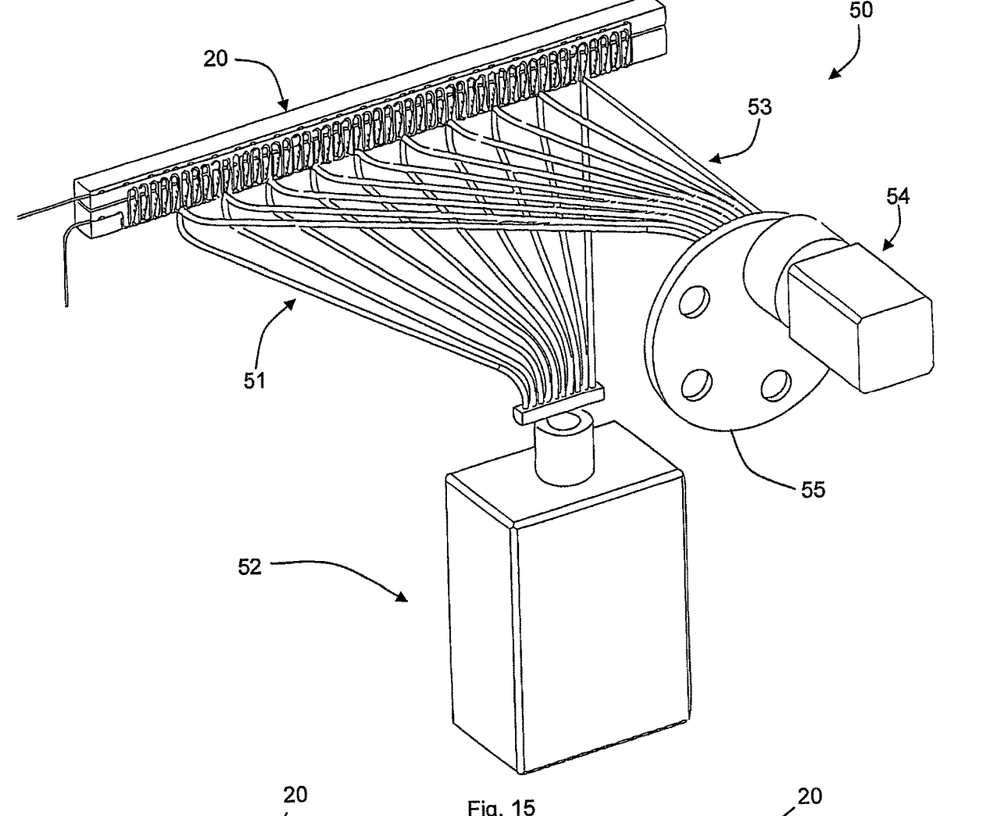
FIGS. 15 and 16 are perspective views showing image capture via optic fibres.
Figure 16:
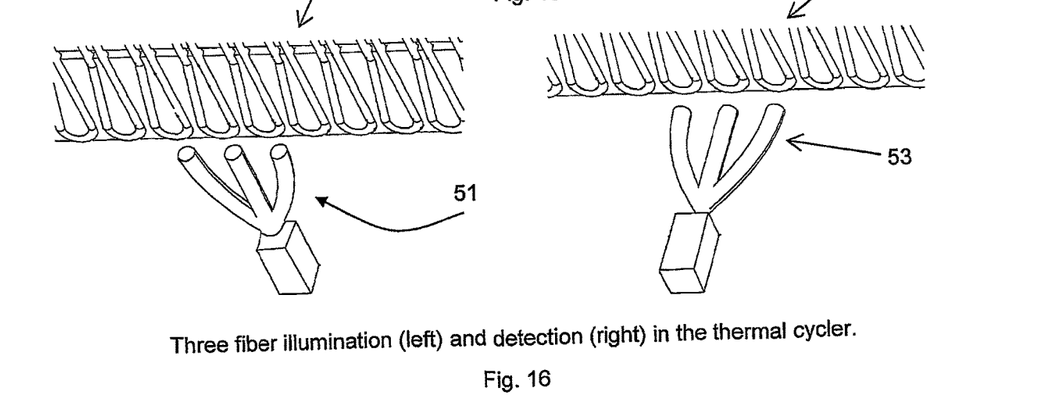
Figure 19:
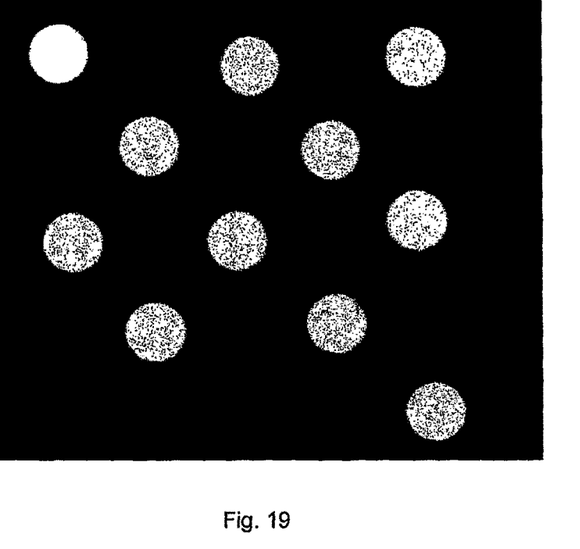
FIG. 19 is a sample image of part of a detector array captured from the thermal cycler of FIG. 17.

FIGS. 15 and 16 show another quantitative detection configuration, 50. Optical fibers are placed at each loop of the tubing in the block. A set of fibers 51 are placed vertically below the thermal cycler 20 and the fiber ends are perpendicular to the tubing. This bundle is attached to a light source 52 which excites the fluorescent particles contained in the droplets as they pass the fiber ends. Another bundle of fibers, 53, are placed horizontally at the front of the thermal cycler with the fiber ends perpendicular to the tubing. This fiber bundle 53 collects the emitted light from the fluorescent particles in the droplet as they pass the fiber ends. The other end of the fiber bundle is detected by a camera 54 for detection of the droplet fluorescence. An example of a detected fiber array is shown in FIG. 19. The continuous acquisition of the fiber bundle image provides the quantitative detection of droplet fluorescence at each individual fiber position. A filter wheel 55 may be used for alternative detection of different fluorescent probes. For example, there are probes with excitation wavelengths which are appropriate to use the same excitation source. However, different detection bandwidths will enable the detection of different probes individually. A filter wheel, a spectrometer or an alternative method of wavelength separation will successfully achieve this goal.

Figures 17, 18:
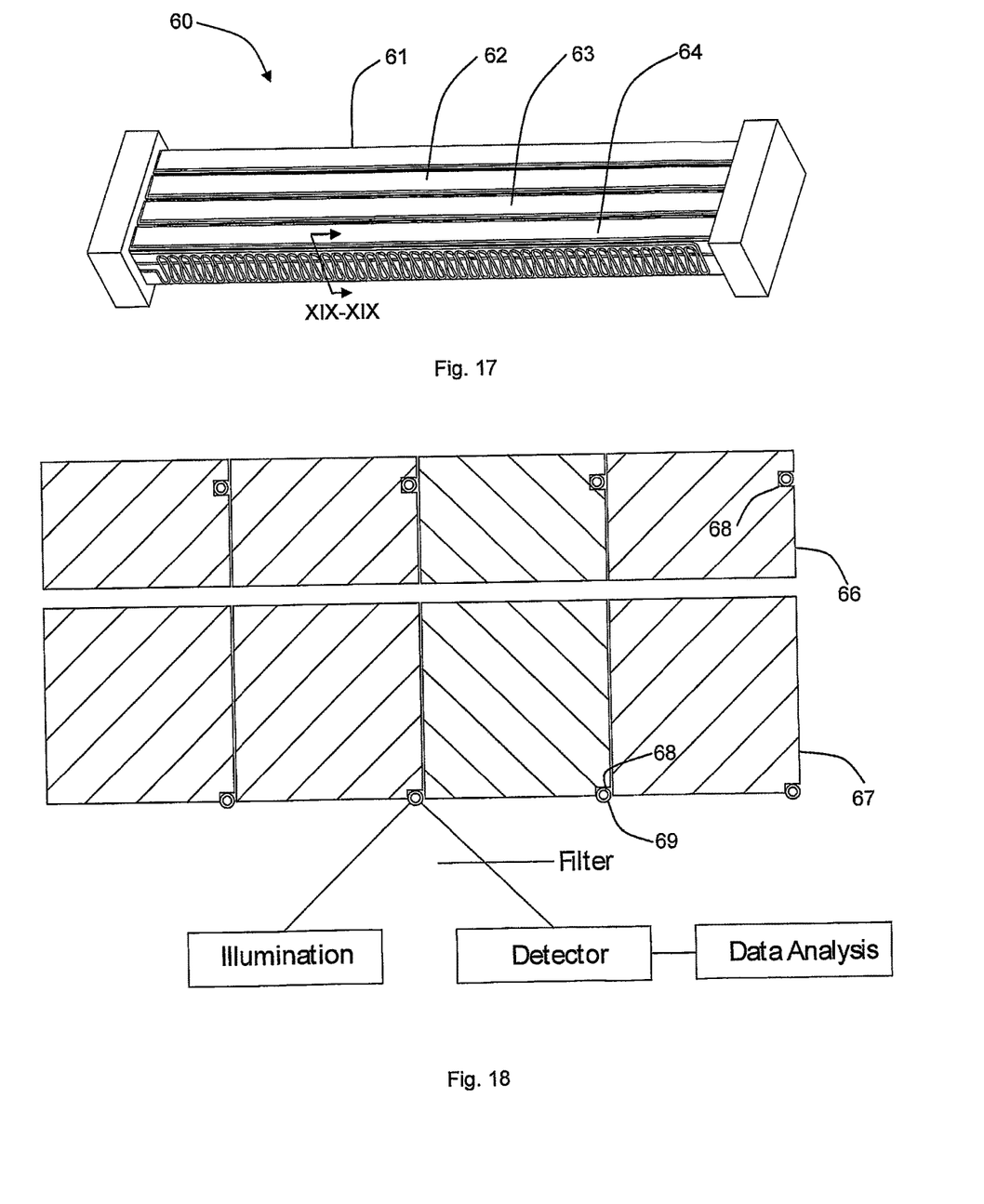
FIG. 17 is a perspective view of a three-dimensional cycler for parallel amplification.
FIG. 18 is a cross-sectional plan view of this cycler.

Referring to FIGS. 17 and 18, the throughput may also be increased by operating a bank 60 of thermal cyclers 61-64 in parallel. A planar system can achieve series sampling of w samples and the parallel configuration can contain y parallel levels. The continuous multi layered thermal cycler 60 results in the product (w x y) sample capability. Such a PCR test of the whole genome of any living form, including the human, could be addressed, which would have applications beyond diagnosis, in many fields of pure and applied science. FIG. 18 shows a part of a cross-section through the cycler, in the direction of the arrows XIX-XIX of FIG. 17. This shows the blocks 66 and 67 and the tubing 68. The tubing where it is exposed provides an array of inspection windows 69.

Figure 20:
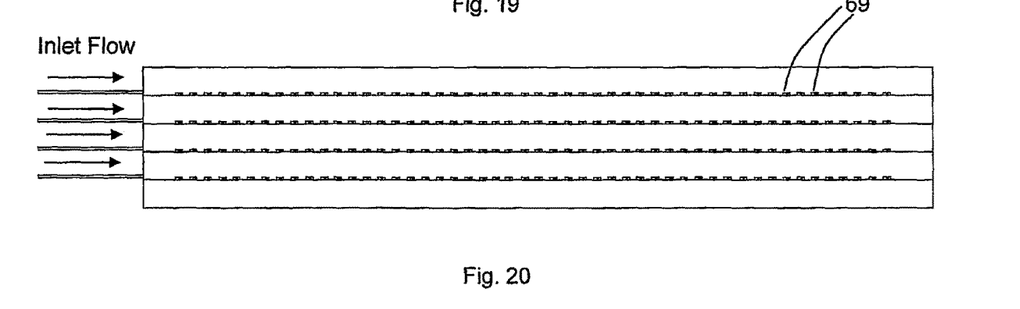
FIGS. 20 and 21 are views of arrays of windows of the cycler of FIG. 17.
Figure 21:
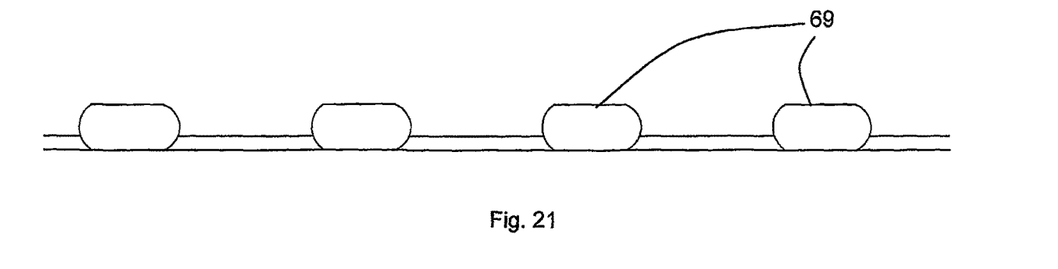

All detection techniques may be applied to a multiple thermal cycler system for quantitative detection. The protruding tubing array for a multiple thermal cycler system, as shown in FIG. 17, can be seen in FIG. 20. FIG. 20 shows inspection windows 69 for a full 4×50 cycle system and FIG. 21 shows a detailed view of a small array of inspection windows 69 more closely. The measurement points may be illuminated by full field illumination or point illumination by high speed scanning or fiber optics. The detection may be carried out the same way, by full field, scanning or simultaneous point detection.

The invention improves upon current well based technology for the quantitative amplification of nucleic acids. In that technology the reagents and sample are loaded into a multi-well plate that is then thermally cycled, with each cycle approximately doubling the target number. The resulting fluorescent intensity increases proportionally so that, with calibration, the amplification can be monitored with time. Standard techniques are then available to calculate the number of targets initially present, which is the required output for qPCR.

In this invention the data set is again three dimensional, monitoring over the x, y plane and with time. The advantage over the well plate is that when plate amplification is complete the plate must be cleaned or disposed with, and a new plate primed and loaded onto the thermal cycling plate. In the invention the data is provided continuously for as long as droplets are fed into the thermal cycler. Because there is no carryover the system can be used continuously.

The geometric arrangement of the capillary tubing in the thermal cycler allows for serial processing, a procession of droplets, parallel processing and an array of closely packed capillary tubes. The rate of production of data is dependant upon the following factors:
1. The droplet length (c. 0.5 mm)
2. The droplet spacing (c. 1.5 mm)
3. The droplet velocity (c. 1 mm/s)
4. The number of parallel lines.

Typical values are given in brackets. The possible degree of parallelism is very great. Using 0.8 mm outside diameter tubing, 100 parallel lines could only take up 80 mm of transverse width.

Using data above, following the time when the first droplets have completed amplification, the system will produce an amplification curve every 0.02 seconds, or 180,000 curves per hour. This is far greater than anything available. Typical high-end systems at present with 384 well plates would need to process 469 plates to achieve the same data set.

The following are some applications of the invention:
Rare target detection
Multiple assay analysis
Multiple sample/assay analysis
End point qualitative detection The invention is not limited to the embodiments described but may be varied in construction and detail. For example, the overall pattern of the flow conduit may not be serpentine. Alternatively, the thermal zones may be thermally controlled by flow of hot water rather than directly by heaters in the hotter zones. Also, a thermoelectric cooler may be used for one or more cooler zones. Further, the flow conduit may not be in a repeated pattern. Instead, it may be straight or curved, passing through a plurality of sets of thermal zones to provide cycles. Also, the detection may not involve fluorescence detection. It may alternatively involve detection of other parts of the electromagnetic spectrum such as change of light polarisation, depending on the desired detection technology.

The invention claimed is:
1. A biological sample analysis system comprising:
a thermal cycling assembly comprising:
a thermally conductive block in thermal communication with one or more heaters, the one or more heaters configured to apply thermal energy to the thermally conductive block to define a plurality of thermal zones, and
a conduit to receive, from a sample preparation system, a plurality of droplets segmented from a biological sample and separated by immiscible carrier fluid, the conduit extending through the thermally conductive block in a serpentine pattern such that the conduit repeatedly passes through each of the plurality of thermal zones of the thermally conductive block,
wherein one or more of a relative number, positioning, or size of each thermal zone of the plurality of thermal zones relative to the conduit is selectively changeable;
a controller operably coupled to the thermal cycling assembly to control the one or more heaters and thereby control a temperature of each thermal zone of the plurality of thermal zones;
a detection system comprising a detector configured to detect light emitted from individual droplets of the plurality of droplets as the individual droplets flow past the detection system; and
a fluid pump operably coupled to the conduit and configured to induce the flow of the plurality of droplets through the conduit and past the detection system.

2. The system of claim 1, wherein the conduit comprises a tube received in a channel.

3. The system of claim 1, wherein the detection system comprises an excitation light source.

4. The system of claim 3, wherein the excitation light source is chosen from a white light source, a laser, and a fiber optic.

5. The system of claim 1, wherein the detector is chosen from at least one of a charged coupled diode (CCD) detector, a complementary metal-oxide semiconductor (CMOS) detector, a photodiode, and a photomultiplier.

6. The system of claim 3, wherein the detection system comprises one or more optical components configured to focus light, or to filter light, or both.

7. The system of claim 1, wherein the detector is configured to detect fluorescence emitted from the plurality of droplets.

8. The system of claim 1, wherein the thermally conductive block comprises aluminum.

9. The system of claim 1, further comprising one or more temperature sensors in thermal communication with each thermal zone, the one or more temperature sensors operably coupled to the controller to provide temperature measurement of each thermal zone to the controller.

10. The system of claim 1, wherein the controller is configured to control the one or more heaters and thereby control the temperature in each thermal zone of the plurality of thermal zones such that the plurality of thermal zones comprises a high temperature zone, a low temperature zone, and a middle temperature zone.

11. The system of claim 1, wherein the controller is configured to control the one or more heaters and thereby control the temperature in each thermal zone of the plurality of thermal zones so as to establish a thermal zone maintained at a first temperature for denaturing nucleic acid, a thermal zone maintained at a second temperature for annealing primers to single-stranded DNA, and a thermal zone for extending the primers in a polymerase reaction to form double-stranded DNA.

12. The system of claim 1, wherein the fluid pump is configured to adjust a velocity of the immiscible carrier fluid to affect a residency time of the plurality of droplets in each thermal zone.

13. The system of claim 1, wherein the one or more heaters comprise a plurality of heaters, at least two thermal zones of the plurality of thermal zones in thermal communication with a respective heater of the plurality of heaters.

14. The system of claim 1, wherein the thermally conductive block is divided into a plurality of thermally conductive block segments, and each thermally conductive block segment has dimensions defined by three pairs of opposite faces.

15. The system of claim 14, wherein the conduit extends along the thermally conductive block adjacent a single face of each of the thermally conductive block segments.

16. The system of claim 1, wherein the controller is configured to independently control the temperature of each thermal zone of the plurality of thermal zones.

17. The system of claim 1, wherein adjacent thermal zones of the plurality of thermal zones are insulated from one another.

18. The system of claim 1, wherein the serpentine pattern lies in a common plane passing through the thermally conductive block.

19. The system of claim 1, wherein the thermally conductive block is in thermal communication with one or more thermoelectric coolers, fluid channels, or both.

20. A biological sample analysis system comprising:
a thermal cycling assembly comprising:
a thermally conductive block in thermal communication with one or more heaters, the one or more heaters configured to apply thermal energy to the thermally conductive block to define first and second thermal zones, and
a conduit to receive, from a sample preparation system, a plurality of droplets segmented from a biological sample and separated by immiscible carrier fluid, the conduit extending through the thermally conductive block in a serpentine pattern and passing through each of the first and second thermal zones so as to flow the plurality of droplets through each of the first and second thermal zones multiple times,
wherein at least one of the first and second thermal zones of the block is moveable in relation to another of the first and second thermal zones of the block;
a controller operably coupled to the thermal cycling assembly to control temperature in each of the first and second thermal zones;
a detection system comprising a detector configured to detect light emitted from individual droplets of the plurality of droplets as the individual droplets flow past the detection system; and
a fluid pump operably coupled to the conduit and configured to induce the flow of the plurality of droplets through the conduit and past the detection system.

21. The system of claim 20, wherein the thermally conductive block is divided into a first thermally conductive block segment and a second thermally conductive block segment corresponding respectively to the first thermal zone and the second thermal zone.

22. The system of claim 20, wherein the controller is configured to control the one or more heaters and thereby control the temperatures of each of the first and second thermal zones.

23. The system of claim 20, wherein the fluid pump is configured to adjust a velocity of the immiscible carrier fluid to affect a residency time of the plurality of droplets in each thermal zone.

24. The system of claim 20, wherein the one or more heaters comprise first and second heaters, the first thermal zone in thermal communication with the first heater and the second thermal zone in thermal communication with the second heater.

25. The system of claim 20, wherein the thermally conductive block has dimensions defined by three pairs of opposite faces, and wherein the conduit extends through the thermally conductive block adjacent a single face of the thermally conductive block.

26. The system of claim 20, wherein the detector is configured to detect fluorescence emitted from the plurality of droplets.

27. The system of claim 20, wherein the thermally conductive block is in thermal communication with one or more thermoelectric coolers, fluid channels, or both.

* * * * *